(12) United States Patent
Zhe et al.

(10) Patent No.: US 12,247,940 B2
(45) Date of Patent: Mar. 11, 2025

(54) FLUID PROPERTY SENSING ARRAY UTILIZING A NEURAL NETWORK

(71) Applicants: Jiang Zhe, Copley, OH (US); Dian Jiao, Akron, OH (US); Aaron Urban, Cleveland, OH (US)

(72) Inventors: Jiang Zhe, Copley, OH (US); Dian Jiao, Akron, OH (US); Aaron Urban, Cleveland, OH (US)

(73) Assignee: THE UNIVERSITY OF AKRON, Akron, OH (US)

(*) Notice: Subject to any disclaimer, the term of this patent is extended or adjusted under 35 U.S.C. 154(b) by 589 days.

(21) Appl. No.: 17/587,101

(22) Filed: Jan. 28, 2022

(65) Prior Publication Data

US 2022/0317081 A1 Oct. 6, 2022

Related U.S. Application Data

(60) Provisional application No. 63/167,827, filed on Mar. 30, 2021.

(51) Int. Cl.
*G01N 27/30* (2006.01)
*G01N 33/28* (2006.01)
(Continued)

(52) U.S. Cl.
CPC ....... *G01N 27/302* (2013.01); *G01N 33/2847* (2013.01); *G01N 33/2876* (2013.01);
(Continued)

(58) Field of Classification Search
None
See application file for complete search history.

(56) References Cited

U.S. PATENT DOCUMENTS

| 7,581,434 B1 | 9/2009 | Discenzo et al. |
| 10,119,927 B2 | 11/2018 | Naide et al. |

(Continued)

OTHER PUBLICATIONS

X. Zhu, et al., "A microsensor array for quantification of lubricant contaminants using a back propagation artificial neural network", Journal of Micromechanics and Microengineering, 26(6): paper 065005, 10 pages, Apr. 2016.*

(Continued)

*Primary Examiner* — J. Christopher Ball
(74) *Attorney, Agent, or Firm* — RENNER KENNER GREIVE BOBAK TAYLOR & WEBER (57) ABSTRACT

A fluid property sensing array includes a first sensor including a first electrode assembly and a first sensing layer at least partially coating the first electrode assembly, the first sensor having a first response to a property of the fluid; and a second sensor including a second electrode assembly and a second sensing layer at least partially coating the second electrode assembly, the second sensor having a second response to the property of the fluid. The array can include a third sensor including a third electrode assembly and a third sensing layer at least partially coating the third electrode assembly, the third sensor having a third response to the property of the fluid. The first sensing layer, the second sensing layer, and the third sensing layer can be compositionally different, such that the first response, the second response, and the third response to the property of the fluid are different.

16 Claims, 3 Drawing Sheets

(51) Int. Cl.
    *G06N 3/04*      (2023.01)
    *G06N 3/063*     (2023.01)
    *G06N 3/08*      (2023.01)

(52) U.S. Cl.
    CPC .............. *G06N 3/04* (2013.01); *G06N 3/063* (2013.01); *G06N 3/08* (2013.01)

(56) References Cited

U.S. PATENT DOCUMENTS

| | | |
|---|---|---|
| 10,365,239 B2 | 7/2019 | Lilik et al. |
| 11,175,274 B2 | 11/2021 | Zhang et al. |
| 11,513,111 B2 | 11/2022 | Patel et al. |
| 11,674,838 B2 | 6/2023 | Brewer et al. |
| 11,796,362 B2 | 10/2023 | Theuveny et al. |
| 2022/0120727 A1 | 4/2022 | Al-Dabbagh et al. |

OTHER PUBLICATIONS

M.F. Smiechowski, et al., "Iridium oxide sensor for acidity and basicity detection in industrial lubricants", Sensors & Actuators B: Chemical, 96(1-2): p. 261-267, Nov. 2003.*

* cited by examiner

FLUID PROPERTY SENSING ARRAY UTILIZING A NEURAL NETWORK

CROSS-REFERENCE TO RELATED APPLICATIONS

This application claims the benefit of U.S. Provisional Application No. 63/167,827, filed on Mar. 30, 2021, which is incorporated herein by reference.

STATEMENT REGARDING FEDERALLY SPONSORED RESEARCH OR DEVELOPMENT

This invention was made with government support under IIP 1940879 awarded by the National Science Foundation. The government has certain rights in the invention.

FIELD OF THE INVENTION

Embodiments of the present invention relate to a fluid property sensing array. One or more embodiments relate to a fluid (e.g. lubricant oil) property sensing array that utilizes a neural network (e.g. general regression neural network).

BACKGROUND OF THE INVENTION

The productivity and lifespan of machinery in a wide variety of industries are highly dependent on proper oil lubrication. As lubricant oil degrades through use, it gradually loses lubrication functionality, which results in damage to a machine. More importantly, a sudden change of lubricant properties may cause catastrophic machine failure. While certain machines recommend interval-based oil changes (e.g. after a set number of miles in a car) to maintain desired machine performance, this estimative approach can be expensive, or cause damage to large machines such as wind turbines, reciprocating compressors, and CNC machines.

Viscosity is the leading parameter in indicating the functionality and longevity of a lubricant oil. Many sensors have been developed for online detection of viscosity, including micro machined cantilever sensors, acoustic sensors, and ratiometric fluorescent sensors. However, while viscosity can be measured independently, the change in viscosity could be caused by a change in a different oil property.

While these different oil properties can be measured precisely in laboratories offline, the offline approach is time consuming and expensive considering the one to two week shipping and analysis time. Thus, others have worked on sensors to monitor the individual oil properties online.

In one example, the oil characteristics associated with oxidation were evaluated using a micro acoustic sensor. However, this sensor was not able to detect bulk changes caused by additives found in lubricant oils.

Other efforts have utilized electrochemical sensors to measure TAN/TBN of oil samples. A problem with these efforts is these sensors relied on chemical reactions between the sensing materials and the contents of oils, which greatly shortens the lifespan of the sensor, making them unsuitable for prolonged and continuous measurements.

In another example, a micro sensor array with individual sensors was developed that determined acid and water content. However, since this array correlated the raw data of the sensor to various properties, it required detailed information such as oil formulation, viscosity, and dielectric constant in order to evaluate the status of the lubricant oil.

Another effort saw the development of an electrochemical sensor array to detect multiple oil properties. Due to the long standing cross sensitivity problem of electrochemical sensors (i.e. each sensor not only responds to the target property but other properties in the oil as well), this sensor array had difficulty in providing accurate TAN/TBN predictions.

There remains a need in the art for an improved oil property sensing array.

SUMMARY OF THE INVENTION

An embodiment of the present invention provides a fluid property sensing array for detecting properties of a fluid, the fluid property sensing array including a first sensor including a first electrode assembly and a first sensing layer at least partially coating the first electrode assembly, the first sensor having a first response to a property of the fluid; a second sensor including a second electrode assembly and a second sensing layer at least partially coating the second electrode assembly, the second sensor having a second response to the property of the fluid; and a third sensor including a third electrode assembly and a third sensing layer at least partially coating the third electrode assembly, the third sensor having a third response to the property of the fluid; where the first sensing layer, the second sensing layer, and the third sensing layer are compositionally different, such that the first response, the second response, and the third response to the property of the fluid are different.

Another embodiment of the present invention provides a fluid property sensing system including the fluid property sensing array, the fluid property sensing system further including a measurement circuit for measuring the first response, the second response, and the third response, to thereby produce a data output; a data acquisition machine for converting the data output into a computer input; and a computer receiving the computer input.

Another embodiment of the present invention provides a method for detecting properties of the fluid, the method implementing the fluid property sensing system, the method including steps of providing the fluid property sensing system; allowing the fluid to flow to the fluid property sensing array; and processing the first response, the second response, and the third response with the computer, the processing step employing a neural network.

DETAILED DESCRIPTION OF ILLUSTRATIVE EMBODIMENTS

Advantages of the present invention will become better understood with regard to the following description, appended claims, and accompanying drawings wherein:

DETAILED DESCRIPTION OF ILLUSTRATIVE EMBODIMENTS

Embodiments of the present invention relate to a fluid property sensing array. One or more embodiments relate to a lubricant oil property sensing system that utilizes a neural network (e.g. general regression neural network). The fluid property sensing array can be within the overall fluid property sensing system for online monitoring of a fluid. Online monitoring of multiple properties of fluids (e.g. lubricant oil) is critical, such as for maintaining and extending the health of highspeed rotating and reciprocating machinery, which machinery is used in many key industries, such as aerospace, manufacturing, and energy. While conventional efforts have been made in this regard, these efforts have struggled with the long-standing challenge of the cross sensitivity that is a product of the overlapping output problem.

Advantageously, one or more embodiments of the present invention provide a capacitive oil property sensor array based on a general regression neural network (GRNN) for measuring acid, base, and water content in lubricant oil. The oil property sensor array, particularly the neural network thereof, is able to pinpoint individual oil properties from the overlapped responses of the various sensors with high accuracy and speed. As further advantages, online oil condition monitoring offered by one or more embodiments of the present invention allows for one or more of detecting multiple oil properties, predicting the remaining life of the lubricant, determining the optimal oil change intervals, avoiding pending machine failures, and reducing maintenance cost.

Figure 1:
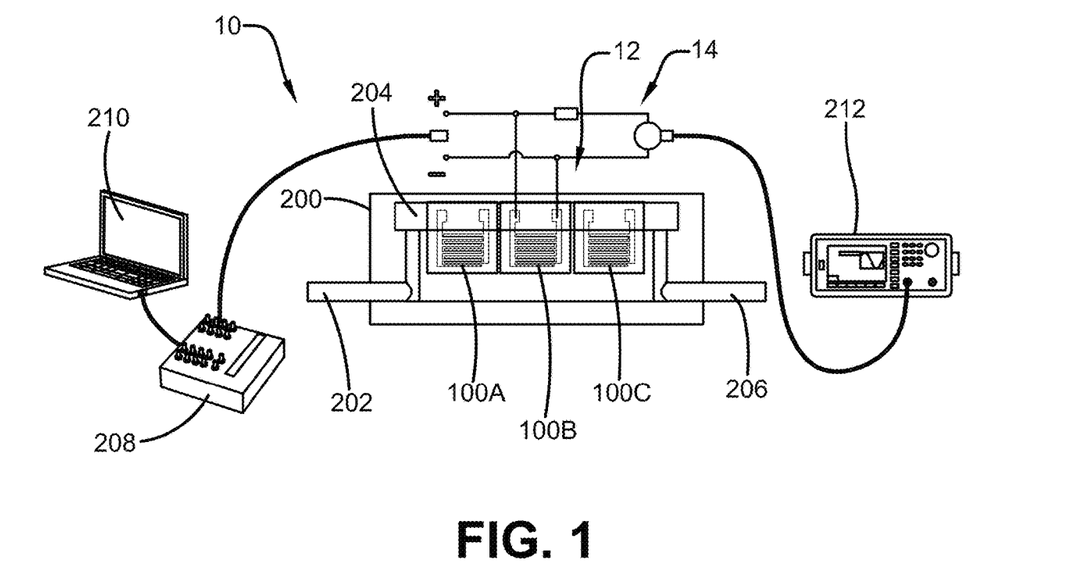
FIG. 1 is a schematic of an oil property sensing system according to one or more embodiments of the invention, showing an oil property sensing array of the oil property sensing system in an online monitoring setup.

With reference to FIG. 1, a fluid property sensing system 10 is shown. The fluid property sensing system 10 includes a fluid property sensing array 12, which may also be referred to as an oil property sensing array 12, a property sensing assembly 12, or a sensor array 12, having a plurality of individual sensors 100A, 100B, 100C. While specific sensors 100A, 100B, 100C are shown in FIG. 1, and will be described herein, the individual generalized sensors are also shown by the numeral 100 in FIG. 2, FIG. 3, and FIG. 4. Therefore, reference may be made herein to the plurality of sensors as being sensors 100.

Within sensor array 12, a first sensor 100A has a first response to one or more properties of a fluid (e.g. lubricant oil), a second sensor 100B has a second response to one or more properties of the fluid, and a third sensor 100C has a first response to one or more properties of the fluid. The first response may include a response to water content and a response to one or more of acid content and base content. The second response may include a response to one or more of acid content and base content with an indifference response, which may also be referred to as a non-response, to the water content. The third response may include a response to both acid content and base content, and the third response may be primarily to the acid content and base content. As will be discussed further herein below, the configuration of the specific sensors 100A, 100B, 100C should be such that the combination of responses allows for distinction between adjustments in one or more properties of the fluid (e.g. lubricant oil), where exemplary properties include acid content, base content, and water content. The specific sensors 100A, 100B, 100C may be in any order so long as they are all immersed in the fluid in the operative configuration.

Figure 2:
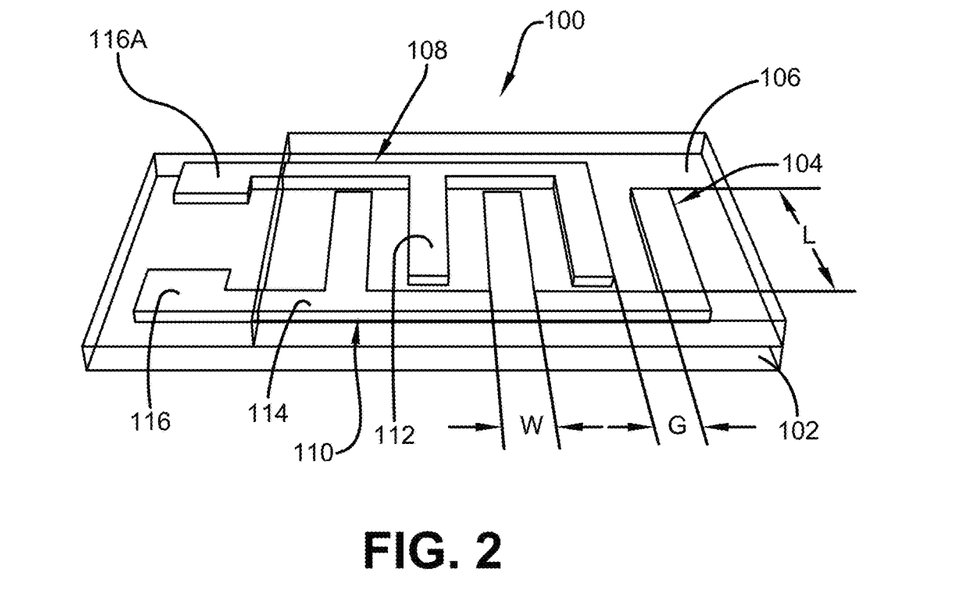
FIG. 2 is a perspective view of a schematic of a sensor of the oil property sensing array according to one or more embodiments of the invention.
Figure 3:
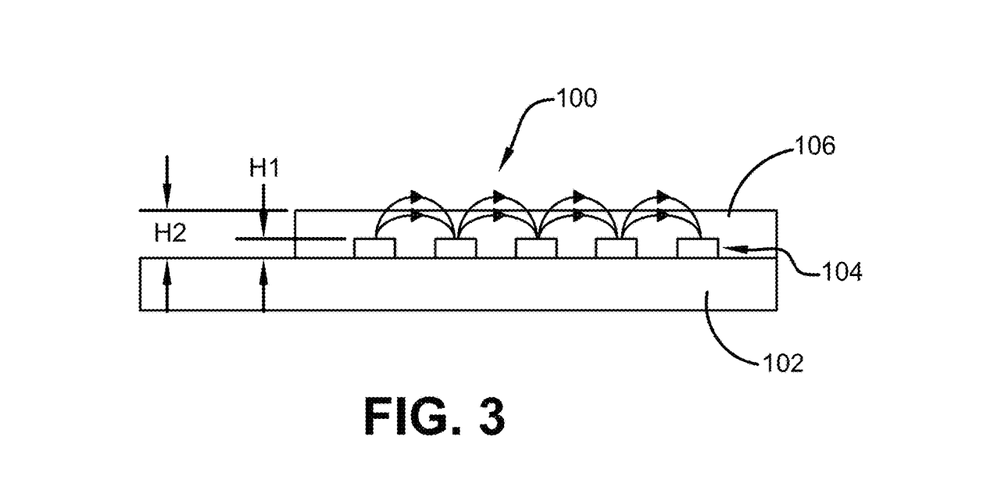
FIG. 3 is a cross-sectional side view of the sensor of FIG. 2.
Figure 4:
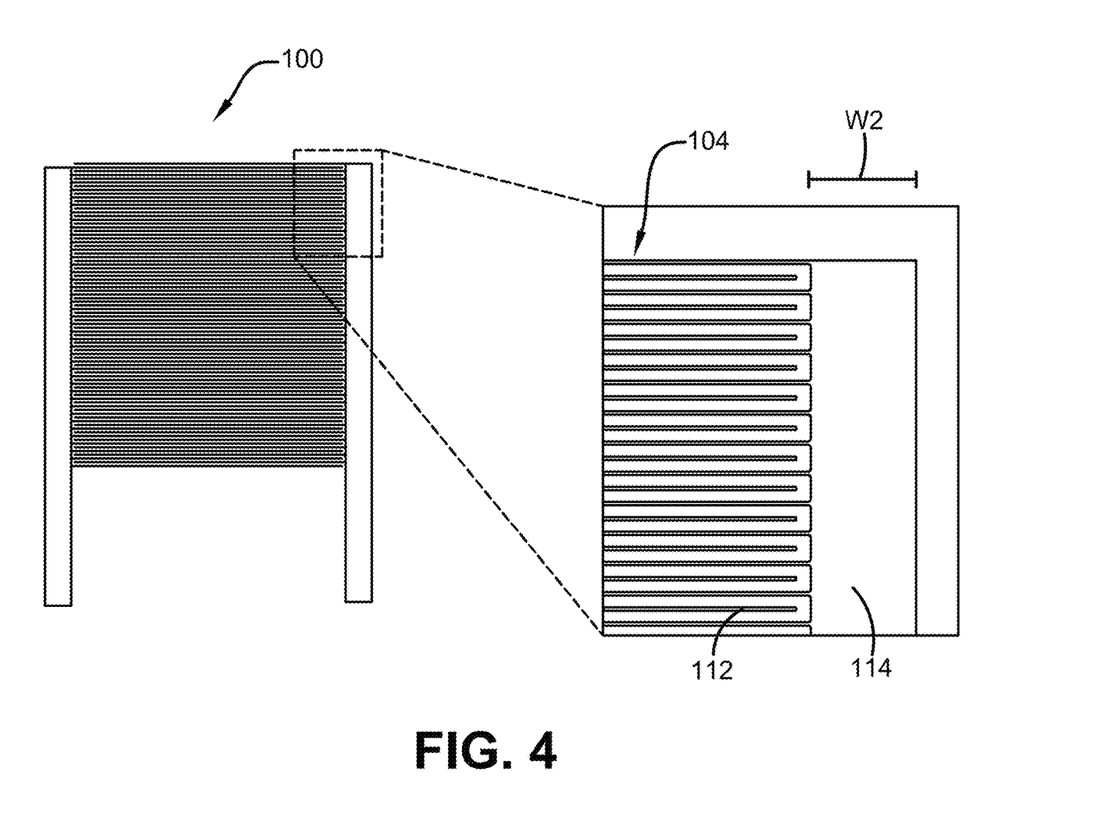
FIG. 4 is a top view of an alternative schematic of a sensor of the oil property sensing array according to one or more embodiments of the invention, showing a microscopic representation of interdigital electrodes of the sensor.

Aspects of the individual sensors 100 are shown across FIGS. 2-4. Sensor 100, which may be referred to as a capacitive sensor 100, includes a base substrate 102 that carries an electrode assembly 104 partially embedded within a coating 106, which may be referred to as an absorbent coating 106 or a sensing layer 106. Base substrate 102 may also be referred to as a piezoelectric substrate 102 and may be made of glass or another suitable material.

It should be appreciated that FIG. 2 and FIG. 4 show the coating 106 as being transparent for the purpose of electrode assembly 104 being viewable through coating 106. In other embodiments, coating 106 is not transparent. The optical properties of coating 106 will depend on the specific material utilized for coating 106.

With specific reference to FIG. 2, electrode assembly 104, which may also be referred to as an interdigitated electrode assembly 104 or interdigital transducer 104, includes a first electrode assembly 108 and a second electrode assembly 110. First electrode assembly 108 and second electrode assembly 110 are individually addressable and include comb-like interdigitated fingers 112 (with the interdigitated descriptor being relative to the fingers 112 of the other electrode assembly 108, 110) that extend from a base 114. Base 114 of first electrode assembly 108 extends to a sensing end 116 and base 114 of second electrode assembly 110 extends to a second sensing end 116A. As shown in FIG. 1, sensing end 116 and second sensing end 116A can be coupled with a measurement circuit 14 for particular analysis of a fluid (e.g. lubricant oil).

As mentioned above, sensors 100 are capacitive sensors. That is, the interdigitated electrode assembly 104 form capacitors, and changes in the capacitance can be attributed to dielectric changes of the fluid (e.g. lubricant oil) between the fingers 112. Sensor 100 can be fabricated using standard photolithography processes followed by a spin coating, or by other suitable techniques.

Electrode assembly 104 may be made of gold or another suitable material. As shown in FIG. 3, electrode assembly 104 has a height H1 above substrate 102. In one or more embodiments, height H1 of electrode assembly 104 can be from 75 nm to 250 nm, in other embodiments, from 5 nm to 25 nm, and in other embodiments, from 40 nm to 80 nm. In one or more embodiments, height H1 of electrode assembly 104 can be about 50 nm, in other embodiments, about 100 nm, and in other embodiments, about 10 nm.

In order to assist with the adhesion between electrode assembly 104 and substrate 102, an adhesion layer (not shown) may be utilized between electrode assembly 104 and substrate 102. The adhesion layer may include one or more of titanium and chromium or another suitable material. An exemplary commercial material for adhesion layer is TA134 from EMF Corporation. In one or more embodiments, the height of adhesion layer can be from 5 nm to 10 nm, in other embodiments, from 20 nm to 30 nm, and in other embodiments, from 2 nm to 20 nm. In one or more embodiments, the height of adhesion layer can be about 3 nm, in other embodiments, about 5 nm, and in other embodiments, about 20 nm.

As mentioned above, electrode assembly 104 includes first electrode assembly 108 and second electrode assembly 110, each having fingers 112 extending from base 114. In one or more embodiments, both of first electrode assembly 108 and second electrode assembly 110 include from 25 to 50 fingers 112, in other embodiments, from 50 to 100 fingers 112, and in other embodiments, from 4 to 15 fingers 112. In one or more embodiments, both of first electrode assembly 108 and second electrode assembly 110 include about 32 fingers 112, in other embodiments, about 40 fingers 112, and in other embodiments, about 96 fingers 112. Said another way, these amounts of fingers 112 are the number of pairs of fingers 112.

In one or more embodiments, the length L of fingers 112 can be from 250 µm to 500 µm, in other embodiments, from 1000 µm to 2000 µm, and in other embodiments, from 5 mm to 1 cm. In one or more embodiments, the length L of fingers 112 can be about 1500 µm, in other embodiments, about 5 mm, and in other embodiments, about 300 µm.

In one or more embodiments, the width W of fingers 112 can be from 1 µm to 5 µm, in other embodiments, from 10 µm to 50 µm, and in other embodiments, from 250 µm to 750 µm. In one or more embodiments, the width W of fingers 112 can be about 3 µm, in other embodiments, about 25 µm, and in other embodiments, about 500 µm.

In one or more embodiments, the gap G between fingers 112 can be from 1 µm to 5 µm, in other embodiments, from 10 µm to 50 µm, and in other embodiments, from 250 µm to 750 µm. In one or more embodiments, the gap G between fingers 112 can be about 4 µm, in other embodiments, about 50 µm, and in other embodiments, about 500 µm.

In one or more embodiments, the width W2 (FIG. 4) of base 114 can be from 250 µm to 750 µm, in other embodiments, from 10 µm to 100 µm, and in other embodiments, from 1000 µm to 2000 µm. In one or more embodiments, the width W2 of base 114 can be about 25 µm, in other embodiments, about 500 µm, and in other embodiments, about 1 mm.

As shown in FIG. 1, oil property sensing array 12 can include different individual sensors 100; namely, first sensor 100A, second sensor 100B, and third sensor 100C. As mentioned above, the different sensors 100A, 100B, 100C are adapted to respond differently to adjustments to one or more properties of a fluid such as lubricant oil.

In order to measure these various properties, the different sensors 100A, 100B, 100C can have similar structural designs (that is, in accord with sensor 100) but have different absorbent coatings 106. That is, the coatings 106 for the different sensors 100 (e.g. sensors 100A, 100B, 100C) can be compositionally different. The specific unique coating 106 utilized for each of the different sensors 100A, 100B, 100C may be such that each sensor 100A, 100B, 100C is more sensitive to one property than other properties. In this way, each sensor 100A, 100B, 100C will respond to different properties with different weights. As will be discussed further herein below, the height H2 (FIG. 3) of absorbent coating 106 may vary for the different sensors 100A, 100B, 100C in order to assist with providing the varying sensitivities to different properties.

The ability of oil property sensing array 12 to monitor these various properties can, for example, help identify the causes of lubricant degradation and/or possible machine failure. Online monitoring of these key properties can, for example, enable optimal oil change intervals and avoid sudden machine failure.

While reference is made in certain instances herein to an oil property sensing array 12 having three different sensors 100A, 100B, 100C, in other embodiments, other suitable numbers of different sensors may be utilized. In one or more embodiments, two sensors 100 are utilized, in other embodiments, four sensors 100 are utilized, and in other embodiments, five sensors 100 are utilized.

As mentioned above, first sensor 100A may include a response to water content and a response to one or more of acid content and base content. Said another way, first sensor 100A may be designed to have an increased response to water. To achieve this function, coating 106 may be a material that absorbs water but rejects lubricant oil. Exemplary coatings 106 that absorb water but reject lubricant oil are polyimide, a sulfonated tetrafluoroethylene-based fluoropolymer-copolymer (Nafion™, e.g. Nafion D-521), and graphene oxide. First sensor 100A primarily responds to the water content but may also respond to another property change of the fluid (e.g. acid content, base content).

In first sensor 100A, as well as other sensors 100 (e.g. sensors 100B, 100C), the response to any particular one or more properties of the fluid is generally based on which components of the fluid are absorbed by the sensing layer 106, thereby causing a change in capacitance for the sensor. That is, for sensor 100A, the molecules of any acid, base, and water are generally absorbed by sensing layer 106 thereby causing the corresponding response based on the change in capacitance. Information may also be gleaned from which components of the fluid are not absorbed by sensing layer 106 of the sensor.

In one or more embodiments, height H2 of coating 106 for first sensor 100A can be from 1 µm to 10 µm, in other embodiments, from 50 nm to 200 nm, and in other embodiments, from 10 µm to 50 µm. In one or more embodiments, height H2 of coating 106 for first sensor 100A can be about 100 nm, in other embodiments, about 4 µm, and in other embodiments, about 25 µm.

Relative to first sensor 100A, as well as other sensors 100 (e.g. sensors 100B, 100C), the fluid generally must be in contact with (e.g. sensor immersed in fluid) or in close proximity to the sensor. Said another way, the strength of the electric field can generally be neglected beyond a vertical distance of λ=(W+G), where λ represents the vertical distance from the IDE/electrode assembly 104 surface, W represents the finger width W (FIG. 2), and G represents the finger gap G (FIG. 2). Changes of the fluid beyond this distance may have no effect or negligible effect on the response of the sensor. In a similar manner, the height H2 of coating 106 might be limited to less than λ/2 in order to achieve the preferred response for the sensor.

As mentioned above, second sensor 100B may include a response to one or more of acid content and base content with an indifference response to the water content. To achieve this function, coating 106 may be a hydrophobic material that resists the absorption of water. Exemplary coatings 106 that resist the absorption of water are polytetrafluoroethylene (PTFE) (Teflon™) and perfluoroalkyl materials. Therefore, second sensor 100B may generally respond to all property changes in the fluid, while remaining largely indifferent to changes of water content within the fluid.

In one or more embodiments, height H2 of coating 106 for second sensor 100B can be from 15 µm to 25 µm, in other embodiments, from 200 µm to 300 µm, and in other embodiments, from 10 µm to 100 µm. In one or more embodiments, height H2 of coating 106 for second sensor 100B can be about 15 µm, in other embodiments, about 70 µm, and in other embodiments, about 300 µm.

As mentioned above, third sensor 100C may include a response to both acid content and base content. To achieve this function, coating 106 may be a material that generally acts as a cation exchange membrane. Exemplary coatings 106 that function as a cation exchange membrane are a sulfonated tetrafluoroethylene-based fluoropolymer-copolymer (Nafion™, e.g. Nafion D-521) and polyester cloth. Therefore, third sensor 100C may generally respond to acid content and base content, and in a manner different from first sensor 100A.

In one or more embodiments, height H2 of coating 106 for third sensor 100C can be from 100 nm to 500 nm, in other embodiments, from 4 μm to 10 μm, and in other embodiments, from 20 nm to 140 nm. In one or more embodiments, height H2 of coating 106 for third sensor 100C can be about 5 μm, in other embodiments, about 250 nm, and in other embodiments, about 80 nm.

As mentioned above, acid content is one property that can give insight regarding the degradation of an oil. Acidic byproducts are formed from oil oxidation, one of the primary causes for oil degradation and unwanted increases in viscosity. Thus, monitoring acid content can provide information on the oxidation process. In one or more embodiments, acid number increases of around 0.3 mg KOH/g may give rise to an alarm for industrial lubricants, in other embodiments, from about 0.2 mg KOH/g to 0.4 mg KOH/g, and in other embodiments, from about 0.25 mg KOH/g to about 0.35 mg KOH/g.

As mentioned above, base content is another property that can give insight regarding the degradation of an oil. Many lubricant oils contain a base additive to neutralize the acid byproducts and slow the oxidation process. As this base reserve depletes, the rate of oxidation will tend to increase. By comparing the trends of the base content with that of the acid content, a more complete picture of the remaining useful life of the oil can be generated. In one or more embodiments, an alarm might exist when base levels deplete to lower than 2 mg KOH/g, in other embodiments, lower than 3 mg KOH/g, and in other embodiments, lower than 1.5 mg KOH/g.

As mentioned above, water content is another important property that can give insight into the status of an oil. The presence of water in a lubricant oil can increase oxidation rates and cause rust and corrosion of machine surfaces. In one or more embodiments, water content of 1000 ppm may be considered to be an alarming amount, in other embodiments, 500 ppm, and in other embodiments, 2000 ppm.

In addition to, or in alternative to, acid content, base content, and water, in one or more embodiments, sensors 100A, 100B, 100C may be adapted to respond to other properties. Exemplary other properties may include soot content, sulfur content, glycol content, ion content of various ions, fuel contamination, nitrogen content, and ash content. In one or more embodiments, additional sensors may be added (that is, in addition to sensors 100A, 100B, 100C) to the sensor array 12 for responding to one or more of the other properties. In one or more embodiments, sensors 100A, 100B, 100C may be adapted to respond to one or more of the other properties.

In one or more embodiments, sensor array 12 consists essentially of first sensor 100A, second sensor 100B, and third sensor 100C, which may be described as only including those components necessary for monitoring lubricant oil and/or as lacking those components that would otherwise be deemed unnecessary for monitoring lubricant oil. In one or more embodiments, sensor array 12 consists of first sensor 100A, second sensor 100B, and third sensor 100C.

While reference is made herein to certain embodiments where the fluid property sensing array 12 is utilized with lubricant oil, the fluid property sensing array 12 may also be suitable for analyzing and monitoring other fluids. This may include adapting the specific sensors 100A, 100B, 100C with coatings 16 suitable for the other fluids. An exemplary other fluid is drinking water. This may include analyzing and monitoring the drinking water relative to safeness for consumption.

As mentioned above, the fluid property sensing system 10 utilizes a neural network. That is, the responses from fluid property sensing array 12 are utilized in conjunction with the neural network. For online monitoring of a fluid utilizing sensor array 12, since there still may be certain cross sensitivities among the sensors 100 (e.g. sensors 100A, 100B, 100C), the responses from the sensors 100 can be sent through the neural network in order to decipher the overlapping responses from the sensors 100 of the sensor array 12. As will be further discussed below, the neural network is implemented as part of a code, which may also be referred to as software, as part of a computer of fluid property sensing system 10. Advantageously, the use of the neural network may enable simplification of training procedures, while also accurately and continuously monitoring the properties (e.g. acid, base, and water contents) of the fluid.

Neural networks generally include a collection of connected nodes, which may be referred to as artificial neurons. The neurons generally model the neurons in a biological brain. Each connection between nodes can transmit a signal to other nodes. Having received a signal, the nodes can process the signal and correspondingly signal neurons connected thereto. The output of each node can be computed by a function of the sum of the inputs. Each connection may be referred to as an edge, and the nodes and edges may have a weight that adjusts with additional learning by the neural network. This adjustable weight may increase or decrease the strength of a signal at a connection. The nodes may be provided with a certain signal-triggering threshold. And different layers of nodes may perform different transformations on the respective inputs. The signals travel through the neural network from the first layer (i.e. the input layer) to the last layer (i.e. the output layer), which may include passing multiple times through the layers.

In one or more embodiments, the neural network is a generalized regression neural network (GRNN). That is, the responses from the sensors 100 can be sent through a GRNN in order to decipher the overlapping responses from the sensors of the sensor array 12. A general regression neural network is an artificial neural network that utilizes a single pass algorithm, which may offer certain advantages when compared with other neural networks. For one, a GRNN generally does not require a large data set. A generalized regression neural network has the ability to generate accurate predictions with smaller data sets, which can be an important feature when data is not readily available and is tedious to generate. A GRNN also offers the ability to expand a data set without reestablishing the network, since the GRNN operates with a single forward pass algorithm.

Where utilized, the generalized regression neural network is employed in conjunction with sensor array 12 for online condition monitoring of the fluid. The GRNN assists with detecting the levels of multiple properties of the fluid. By employing a GRNN in conjunction with sensor array 12, the cross sensitivities of the responses of sensors 100 can be removed.

Figure 5:
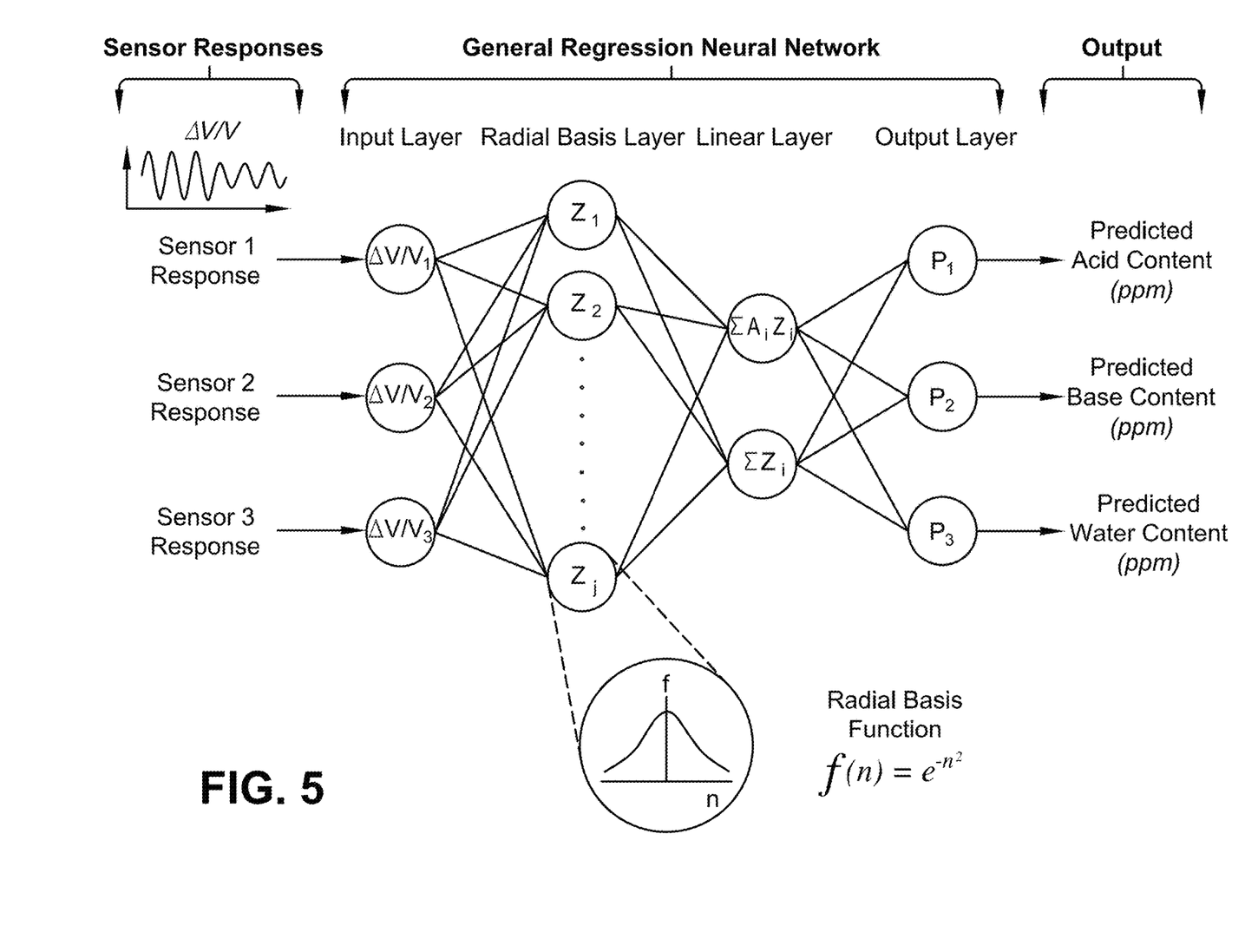
FIG. 5 is a schematic of a general regression neural network (GRNN) architecture for the oil property sensing system according to one or more embodiments of the invention.

A specific GRNN is shown in FIG. 5. The responses of sensors 100 (e.g. sensors 100A, 100B, 100C) are sent to an input layer of the GRNN. In addition to the input layer, the GRNN of FIG. 5 also includes a radial basis layer, a linear layer, and an output layer. Each node, which may be referred to as a neuron, in the input layer represents the relative voltage/capacitance change from one of the sensors 100. Each node in the output layer represents the corresponding property to be determined by the GRNN. FIG. 5 specifically shows the acid content, base content, and water content being determined. The number of nodes (i.e. $z_j$) in the radial basis layer is equal to the number of sample data points used to create the network. Each neuron in the radial basis layer is related to all the neurons in the previous layer via a distance value that is passed through a radial basis function. The linear layer performs a summation function as shown in FIG. 5. This GRNN or another suitable GRNN may be developed using the MatLab™ platform.

For the GRNN, and in order to predict the fluid properties, the Euclidean distance can be first found. The Euclidean distance is the calculation for between the inputs for a data point and the inputs of the whole dataset. The Euclidean distance is defined in Equation (1):

$$\text{Euclidean Distance} = \sqrt{\sum_{i=1}^{n}(x_i - y_i)} \quad \text{Equation (1)}$$

where $x_i$ is the data point's input from the ith sensor, $y_i$ is the input from the ith sensor of a single entry in the GRNN dataset, and n is the number of inputs in the network. This distance is calculated for every entry in the dataset, and this array is multiplied by a scalar bias.

This scalar bias is defined in Equation (2):

$$\text{Bias} = \frac{\sqrt{-\ln 0.5}}{\sigma} \quad \text{Equation (2)}$$

where $\sigma$ is the smoothing factor, a parameter that affects smoothness of the network's prediction curve, as well as the ability to generalize. An optimal smoothing factor may be determined through an iterative process. Exemplary optimal determination processes include the fruit-fly optimization algorithm and the sweeping method (i.e. sweeping a wide range of smoothing factors with a small step).

Each value of the array resulting from multiplying the bias and the distance is passed through a radial basis function, defined in Equation (3):

$$\text{RadialBasis}(n) = e^{-n^2} \quad \text{Equation (3)}$$

where n represents the values of the array resulting from the previous step.

Finally, a normalized dot product between this resulting array and the outputs of the GRNN's data set results in the predicted values, defined in Equation (4):

$$\text{Prediction} = \frac{A \cdot Z}{\sum_{i}^{d} Z_i} \quad \text{Equation (4)}$$

where A is the array of outputs in the GRNN's dataset, Z is the array generated from the previous step, and d is the number of data points in the GRNN's dataset.

Because the GRNN uses forward propagation, it may have advantages compared to other neural networks. For a GRNN, the dataset can simply be expanded with new samples without requiring a new training procedure. This convenience allows for the network to be easily tailored to the requirements of a user. The GRNN may also display better accuracy, especially when sample sizes are relatively small. Also, because it is impractical to generate huge datasets online, the GRNN may be more suitable for online oil condition monitoring.

Any suitable number of nodes of the input layer, nodes of the radial basis layer, nodes of the linear layer, and nodes of the output layer may be utilized. In one or more embodiments, two nodes, in other embodiments, three nodes, in other embodiments, four nodes, and in other embodiments, five nodes, may be utilized for the input layer. In one or more embodiments, ten nodes, in other embodiments, twenty nodes, in other embodiments, thirty nodes, and in other embodiments, thirty-two nodes, may be utilized for the radial basis layer. In one or more embodiments, two nodes, in other embodiments, three nodes, in other embodiments, four nodes, and in other embodiments, five nodes, may be utilized for the linear layer. In one or more embodiments, two nodes, in other embodiments, three nodes, in other embodiments, four nodes, and in other embodiments, five nodes, may be utilized for the output layer. The specific numbers listed here (and elsewhere) may be utilized to form suitable ranges. That is, as an example, one or more embodiments include from ten nodes to twenty nodes for the radial basis layer.

In one or more embodiments, the neural network may be a back-propagation neural network (BPNN). That is, the responses from the sensors 100 can be sent through a BPNN in order to decipher the overlapping responses from the sensors of the sensor array 12. BPNN generally operates by computing the gradient of the loss function with respect to the weights of the network for a single input-output example. The computing of the gradient generally operates under the chain rule, computing the gradient one layer at a time, and iterating backward from the last layer to avoid redundant calculations of intermediate terms. BPNN may require additional training process, which might include additional training data.

In one or more embodiments, the neural network is a radial basis function neural network (RBFNN). Other suitable neural networks may generally be known by or may become known to the skilled person. In one or more embodiments, a singular spectrum analysis can be coupled with the neural network in order to further reduce unwanted noises and increase signal strength.

As mentioned above and as shown in FIG. 1, fluid property sensing array 12 may be included within fluid property sensing system 10. Fluid property sensing system 10 further includes a machine 200 or a machine housing 200 that receives a fluid (e.g. lubricant oil). The fluid flows into machine 200 via a fluid inlet 202, passes through a sensing portion 204 of sensor array 12, and flows out of machine 200 via a fluid outlet 206. Machine 200 or machine housing 200 may be a highspeed rotating and reciprocating machinery, including turbomachines, combustion engines, and heavy equipment. The specific machine housing 200 may be a storage tank for the fluid. Fluid property sensing array 12 may be mounted to a side wall of a storage tank.

Sensing portion 204, which includes sensing ends 116 and second sensing ends 116A (FIG. 2), of sensor array 12 can be coupled with measurement circuit 14 for analysis of the fluid. The measurement circuit 14 measures the responses of the sensors 100 of sensor array 12 to thereby produce a data output. More specifically, the measurement circuit 14 captures the peak values of the AC voltage output from each sensor 100, which can serve to reduce the amount of data to be collected by a data acquisition (DAQ) machine 208 with which measurement circuit 14 is coupled. The measurement circuit 14 is coupled with a data acquisition (DAQ) machine 208 for converting the results from sensor array 12 and measurement circuit 14 into digital numeric values that can be manipulated by a computer 210. An exemplary DAQ machine is PCI-6133 from National Instruments. The recording of the responses from sensor array 12 may include a wait time, such as after 20 minutes. As noted above, changes in the concentrations of various properties in the fluid (e.g. oil) leads to changes in the capacitance of the IDE sensors 100A, 100B, 100C of sensor array 12. This capacitance change correlates with an impedance change of the sensors 100A, 100B, 100C. To measure this change, voltages across the capacitive sensors 100A, 100B, 100C can be recorded with the DAQ machine 208. DAQ machine 208 generally includes suitable sensors, signal conditioning circuitry, and analog-to-digital converters, as generally known to the skilled person.

The DAQ machine 208 is coupled with a computer 210 for manipulation and display of the results. As mentioned above, computer 210 also includes the neural network (e.g. GRNN) within software thereon. Other suitable details for computer 210 will be generally known to the skilled person.

The measurement circuit 14 is further coupled with a function generator 212. Function generator 212 generally serves to generate an electrical waveform, which may be over a range of frequencies. The waveform produced may be a sine wave. An exemplary excitation signal for sensor array 12 is a 2 MHz, 10 $V_{pp}$ sine wave. An exemplary function generator 212 is the 33,600 A Series from Agilent.

For the operative configuration of fluid property sensing system 10, a certain number of samples and data are collected. It may be desirable to employ an under-sampling technique in order to generally reduce the amount of data needed. Where utilized, the under-sampling technique may be used to capture voltage peaks, which can significantly reduce the amount of the collected data. With this reduced amount of data, fluid property sensing system 10 may be more suitable for online fluid condition monitoring. Other details of a suitable under-sampling method may be generally known to the skilled person. In one or more embodiments, with use of an under-sampling method, a sampling rate of 110 kHz may be utilized to capture the peaks of a 2 MHz sine wave signal.

After the raw data is collected (i.e. from sensor array 12), a fast Fourier transform (FFT) may be applied in order to filter out unwanted noises from the raw data. This may include calculating an average peak voltage, and then importing the average peak voltage to the neural network (e.g. GRNN) for calculation of the target properties.

It should be appreciated that the components of fluid property sensing system 10 are in suitable communication with one another, which may be any suitable physical communication or wireless communication, where appropriate.

Since there could be unexpected contaminants in the fluid that are not being measured by the system 10, system 10 may be adapted to ensure these contaminants would not have a major impact on the sensor array 12. An exemplary unexpected contaminant includes wear debris particles in lubricant oil. Wear debris particles include iron and ceramic wear debris. In one or more embodiments, even the presence of an anticipated amount of wear debris may only cause a negligible error (e.g. from 0.2% to 0.5% error from GRNN) in the predicted properties. Exemplary amounts of wear debris particles include a 30 ppm concentration of iron particles and a 40 ppm concentration of ceramic particles. For these amounts, the wear debris particles may be neglected for system 10.

As suggested above, the responses of the capacitive sensors 100 and the changes in the responses are caused by the changes in relative permittivity of the oil. The permittivity change is not directly dependent on machine operating parameters (e.g. rotational speed or torque) but may be affected by other properties (e.g. fluid operating temperature). Thus, in one or more embodiments, system 10 may include one or more additional sensors, such as a temperature sensor, in order to account for changes in these other properties. Though, the data collection of system 10 can generally be performed at the expected operating parameters (e.g. temperature) of the fluid.

EXAMPLE

In one specific set of examples that were performed, 48 oil samples were prepared, where 36 were used for training to determine an optimal smoothing factor, and 12 were used as a final testing dataset. These samples contained varying concentrations of acid, base, and water. Water contents were altered by adding $H_2O$ at concentrations of 500, 1000, and 1500 ppm. Sulfuric acid ($H_2SO_4$) and potassium hydroxide (KOH) were used to change the respective acid and base levels at concentrations of 1000, 2000, 3000, and 4000 ppm. Conventional oil (MAG 1™, Conventional 10 W-30) was used as a foundational oil. These concentrations were chosen to simulate conditions that have been used by industrial lubrication systems.

Individual samples were prepared and thoroughly mixed right before testing to prevent any separation. Samples were loaded into a tank. Three capacitive sensors were installed on a side wall of the tank. Oil was circulated via a pump at a fixed flow rate of 100 mL/min. The excitation signal for the sensors array was a 2 MHz, 10 $V_{pp}$ sine wave via a function generator. Sensor responses were recorded through a DAQ device after 20 min, and sensors were cleaned and dried between testing with different samples.

Changes in the concentrations of various properties in the oil led to changes in the capacitance of the IDE sensors. This capacitance change correlated with an impedance change of the sensor. To measure this change, voltages across the capacitive sensors were recorded with the DAQ. To reduce the amount of data, an under-sampling technique was used to capture voltage peaks, which reduced the amount of the collected data. With the under sampling, a sampling rate of 110 kHz was used to capture the peaks of a 2 MHz sine wave signal.

After the raw data was collected, a fast Fourier transform (FFT) was applied to filter out unwanted noises. The average peak voltage was calculated and was imported to a GRNN to calculate the target properties. The GRNN was developed in MatLab™ using built-in neural network tools and custom code for analysis. The GRNN contained an input layer, a radial basis layer, a linear/pattern layer, and an output layer. The input and output layers had three nodes, corresponding to the number of sensors and number of properties. The radial basis layer contained thirty-two nodes, corresponding to the number of training samples, and the linear layer had two nodes.

The trend for each property was determined. This was done by measuring the responses of the sensors to samples with changes in only one property. For each oil sample, the measurements of the responses were taken at t=20 min after submersion of the sensors. Before the sensors were tested in the next oil sample, the sensors were cleaned and dried. The responses of the sensors to oil samples with varying contents of only one property (water, acid, and base) were plotted.

Each error bar represented standard deviation of three separate measurements of one sample. The collected data met this criteria, as the relative voltage change for acid steadily increased from −0.15% to −0.04% (Teflon™ coated sensor), decreased from −0.2% to −20.9% for base (Nafion™ coated sensor), and decreased from −0.2 to −0.27 for water (Polyimide coated sensor).

Next, the sensors were measured with the 36 training oil samples to train the network and an additional 12 testing samples to evaluate the accuracy of the network. These 48 samples contained different combinations of acid, base, and water contents discussed above. The sensor responses were collected when they were submerged in the oil sample for 20 min. During network training, the training dataset of 36 was randomly divided into 5 groups. A k-fold cross validation method was used on these groups: 4 groups were used for training, while the remaining group was used for validation in determining the optimal smoothing factor. This process was repeated 4 more times until each group was used as the validation group.

After training, the network was tested on the separate testing dataset (12 samples) to determine the performance of the network on data it was not trained with. During training, the network was run for a range of smoothing factors from 0.0001 to 0.5 in steps of 0.00001 in order to determine the optimal value. All errors were normalized to have even weight since the monitored ppm range for the properties were different, and the smoothing factor with the lowest combined normalized error was selected for the network. Data was normalized by multiplying the water error (ppm) by a value of 4000/1500 to account for the difference in range from water to acid/base content.

One focus was to reduce the amount of training samples while keeping satisfactory accuracy, because using a large number of samples for training would be impracticable for onsite oil property monitoring. The training was conducted using varying sizes of training samples—20, 26, and 36. The difference between using the three training samples sizes was found to be negligible. The optimal smoothing factor for the GRNN was found to be 0.0150, 0.0153, and 0.0158, respectively. 0.0150 was used for the subsequent predictions with the 20 sample dataset.

Since data can be iteratively added to the GRNN without a retraining process, the trend of the network's prediction error could be monitored as samples were added to the dataset. By analyzing the average prediction error for each property, samples could be added to whichever property had the highest error to further reduce that error. The average prediction error was calculated by taking the average of the percent errors from each prediction from the test group, as shown in Equation (5):

$$\text{Average Prediction Error} = \frac{\sum E_{test}}{n_{test}} \quad \text{Equation (5)}$$

where $E_{test}$ is the percent error for a single prediction from the test dataset, and $n_{test}$ is the number of datapoints in the test dataset. The average prediction error was collected from the 36 training samples. The average prediction error only decreased a little when the training samples was increased from 20 to 36.

Finally, the network was tested using samples with various concentrations of the acid, base, and water. The samples covered a wide range of property contents: acid from 0 to 4000 ppm, base from 0 to 4000 ppm, and water from 0 to 1500 ppm. These ranges covered critical areas for lubricant functionality in industrial machinery. The average prediction error was collected from the 12 testing samples when the network was trained with different samples sizes. As the training dataset increased from 10 to 20, the average water content error was reduced from 38% to 13%, the average acid error from 14% to 6%, and the average base error from 5% to 3%. A 20-sample training dataset was found to be sufficient. Additional samples only decreased the average prediction error by a small amount. When the dataset was increased from 20 to 36 samples, the error reduction for acid, base, and water content were only 0.72%, 0.05%, and 1.8% respectively.

The predicted contents by the GRNN were compared to the actual contents for the 12 testing samples, which were not used in training. Each sample was measured three times with an interval of two hours. The two sets of values were in good agreement. The maximum percent error for acid, base, and water content was 6.9%, 4.2%, and 15.7% respectively. The comparatively higher prediction error in water content could be attributed to the fact that changes in water content had the smallest corresponding sensor responses in magnitude. This effect was also evident for the base predictions, where the highest sensor response resulted in the smallest error. Based on these results, this sensor array in combination with the GRNN was found to be capable of untangling non-linear and overlapped sensor responses and making accurate predictions of multiple properties of a fluid such as lubricant oil.

The prediction error of this system could be reduced by two approaches. First, the noise from the raw signal, especially for the sensor which had a lower sensitivity, was one of the major sources for the prediction errors. For example, the prediction in water content had a larger average error (14%) than the other properties (6% and 3%). This is because the Teflon™ coated sensor had a low sensitivity to water content change; therefore, the relative amplitude of the noise was larger than that of the other properties. The prediction error could be reduced by using a coating material that generates higher sensitivity to the target property. Reducing the thickness of the sensing material was also found to increase the sensitivity, although the measurement range of the sensor was reduced. Second, adding more training samples, especially at smaller concentration ranges, could potentially reduce the prediction error at the price of a longer training time.

It is worth mentioning here that the fruit-fly optimization algorithm was employed and found to find an optimal smoothing factor in 30 s. The sweeping method took approximately 49 s. All calculations were performed in a Dell Latitude 5420 laptop.

Two additional neural networks, a radial basis network and a back propagation neural network, were also established to make predictions. Both of these networks were established using the MatLab™ neural network toolbox.

The effect of contaminants (e.g. wear debris particles) was analyzed to ensure they would not have a significant impact on the sensors. This was tested for the GRNN prediction by introducing iron and ceramic wear debris into the lubricant oil. A 30 ppm concentration of iron particles resulted in a 0.0038% voltage change, while a 40 ppm concentration of ceramic particles resulted in a 0.0069% voltage change. Such changes would result in approximately a 0.2% and 0.5% error from GRNN, which can be neglected. The concentrations of wear debris were selected based on what would be expected in industrial applications.

In light of the foregoing, it should be appreciated that the present invention significantly advances the art by providing an improved fluid property sensing array. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A fluid property sensing array for detecting properties of a fluid, the fluid property sensing array comprising
a first sensor including a first electrode assembly and a first sensing layer at least partially coating the first electrode assembly, the first sensor having a first response to a property of the fluid;
a second sensor including a second electrode assembly and a second sensing layer at least partially coating the second electrode assembly, the second sensor having a second response to the property of the fluid; and
a third sensor including a third electrode assembly and a third sensing layer at least partially coating the third electrode assembly, the third sensor having a third response to the property of the fluid;
where the first sensing layer, the second sensing layer, and the third sensing layer are compositionally different, such that the first response, the second response, and the third response to the property of the fluid are different;
where the first sensing layer includes polyimide, where the second sensing layer includes polytetrafluoroethylene, and where the third sensing layer includes a sulfonated tetrafluoroethylene-based fluoropolymer-copolymer.

2. The fluid property sensing array of claim 1, where the fluid is lubricant oil.

3. The fluid property sensing array of claim 1, where the first response includes response to water content of the fluid and response to one or more of acid content and base content of the fluid.

4. The fluid property sensing array of claim 3, where the second response includes response to the one or more of acid content and base content of the fluid and an indifference response to the water content of the fluid.

5. The fluid property sensing array of claim 4, where the third response includes response to both the acid content and the base content of the fluid.

6. The fluid property sensing array of claim 2,
where the first response includes response to water content of the lubricant oil and response to one or more of acid content and base content of the lubricant oil,
where the second response includes response to the one or more of acid content and base content of the lubricant oil and an indifference response to the water content of the lubricant oil, and
where the third response includes response to both the acid content and the base content of the lubricant oil.

7. The fluid property sensing array of claim 1, where the first electrode assembly, the second electrode assembly, and the third electrode assembly include respective interdigitated electrode assemblies.

8. A fluid property sensing system comprising
a fluid property sensing array for detecting properties of a fluid, the fluid property sensing array comprising
a first sensor including a first electrode assembly and a first sensing layer at least partially coating the first electrode assembly, the first sensor having a first response to a property of the fluid;
a second sensor including a second electrode assembly and a second sensing layer at least partially coating the second electrode assembly, the second sensor having a second response to the property of the fluid; and
a third sensor including a third electrode assembly and a third sensing layer at least partially coating the third electrode assembly, the third sensor having a third response to the property of the fluid;
where the first sensing layer, the second sensing layer, and the third sensing layer are compositionally different, such that the first response, the second response, and the third response to the property of the fluid are different;
a measurement circuit for measuring the first response, the second response, and the third response, to thereby produce a data output;
a data acquisition machine for converting the data output into a computer input; and
a computer for receiving the computer input, where the computer employs a neural network for processing the computer input, where the neural network is a general regression neural network.

9. The fluid property sensing system of claim 8, where the general regression neural network includes an input layer, a radial basis layer, a linear layer, and an output layer.

10. The fluid property sensing system of claim 9, where the input layer includes from three to five nodes, the radial basis layer includes from ten to thirty-two nodes, the linear layer includes from two to five nodes, and the output layer includes from three to five nodes.

11. The fluid property sensing system of claim 10, where the input layer includes three nodes, and the output layer includes three nodes.

12. A fluid property sensing system comprising
a fluid property sensing array for detecting properties of a fluid, the fluid property sensing array comprising
a first sensor including a first electrode assembly and a first sensing layer at least partially coating the first electrode assembly, the first sensor having a first response to a property of the fluid;
a second sensor including a second electrode assembly and a second sensing layer at least partially coating the second electrode assembly, the second sensor having a second response to the property of the fluid; and
a third sensor including a third electrode assembly and a third sensing layer at least partially coating the third electrode assembly, the third sensor having a third response to the property of the fluid;
where the first sensing layer, the second sensing layer, and the third sensing layer are compositionally different, such that the first response, the second response, and the third response to the property of the fluid are different;
where the system provides a first alarm for an increase in the acid content being about 0.3 mg KOH/g, a second alarm for the base content being lower than 2 mg KOH/g, and a third alarm for the water content being about 1000 ppm.

13. A fluid property sensing system comprising
a fluid property sensing array for detecting properties of a fluid, the fluid property sensing array comprising
a first sensor including a first electrode assembly and a first sensing layer at least partially coating the first electrode assembly, the first sensor having a first response to a property of the fluid;

a second sensor including a second electrode assembly and a second sensing layer at least partially coating the second electrode assembly, the second sensor having a second response to the property of the fluid; and a third sensor including a third electrode assembly and a third sensing layer at least partially coating the third electrode assembly, the third sensor having a third response to the property of the fluid;

where the first sensing layer, the second sensing layer, and the third sensing layer are compositionally different, such that the first response, the second response, and the third response to the property of the fluid are different;

where the system provides a first alarm for an increase in the acid content being from 0.2 mg KOH/g to 0.4 mg KOH/g, a second alarm for the base content being lower than 3 mg KOH/g, and a third alarm for the water content being from 500 ppm to 2000 ppm.

14. A fluid property sensing system comprising
a fluid property sensing array for detecting properties of a fluid, the fluid property sensing array comprising
a first sensor including a first electrode assembly and a first sensing layer at least partially coating the first electrode assembly, the first sensor having a first response to a property of the fluid;
a second sensor including a second electrode assembly and a second sensing layer at least partially coating the second electrode assembly, the second sensor having a second response to the property of the fluid; and
a third sensor including a third electrode assembly and a third sensing layer at least partially coating the third electrode assembly, the third sensor having a third response to the property of the fluid;
where the first sensing layer, the second sensing layer, and the third sensing layer are compositionally different, such that the first response, the second response, and the third response to the property of the fluid are different;
a machine housing containing the fluid property sensing array;
a fluid inlet for passing the fluid into the machine housing; and
a fluid outlet for flowing the fluid out of the machine housing.

15. A method for detecting properties of the fluid, the method implementing the fluid property sensing system of claim 14, the method comprising steps of
providing the fluid property sensing system of claim 14;
allowing the fluid to flow to the fluid property sensing array; and
processing the first response, the second response, and the third response with the computer, the processing step employing a neural network.

16. The method of claim 15, where the neural network is a general regression neural network.

* * * * *